(12) United States Patent
Fransson (10) Patent No.: US 11,730,677 B2
(45) Date of Patent: Aug. 22, 2023

(54) SYRINGE ASSEMBLY WITH ION-EXCHANGE MATERIAL

(71) Applicant: Swedish Orphan Biovitrum AB (publ), Stockholm (SE)

(72) Inventor: Jonas Fransson, Uppsala (SE)

(73) Assignee: SWEDISH ORPHAN BIOVITRUM AB (PUBL), Stockholm (SE)

( * ) Notice: Subject to any disclaimer, the term of this patent is extended or adjusted under 35 U.S.C. 154(b) by 457 days.

(21) Appl. No.: 16/763,286

(22) PCT Filed: Nov. 16, 2018

(86) PCT No.: PCT/EP2018/081588
§ 371 (c)(1),
(2) Date: May 12, 2020

(87) PCT Pub. No.: WO2019/097003
PCT Pub. Date: May 23, 2019

(65) Prior Publication Data
US 2020/0306138 A1    Oct. 1, 2020

(30) Foreign Application Priority Data

Nov. 17, 2017   (EP) .................................. 17202396

(51) Int. Cl.
*A61J 1/20* (2006.01)
*B01J 47/15* (2017.01)
(Continued)

(52) U.S. Cl.
CPC .............. *A61J 1/2003* (2015.05); *A61M 5/19* (2013.01); *A61M 5/3145* (2013.01);
(Continued)

(58) Field of Classification Search
CPC ........ A61J 1/2003; A61M 5/178; A61M 5/19; A61M 5/31; A61M 5/3129; A61M 5/3145;
(Continued)

(56) References Cited

U.S. PATENT DOCUMENTS 5,681,475 A * 10/1997 Lamensdorf .............. C02F 1/76
210/666
5,860,957 A * 1/1999 Jacobsen ............... A61M 5/282
604/140
(Continued)

FOREIGN PATENT DOCUMENTS

AU    2010101255 A4    12/2010
EP        1767243 A1 *  3/2007    ........... A61N 1/0444
(Continued)

OTHER PUBLICATIONS

International Search Report from PCT Application No. PCT/EP2018/081588 dated Feb. 12, 2019.
(Continued)

*Primary Examiner* — Kami A Bosworth
(74) *Attorney, Agent, or Firm* — Harness Dickey & Pierce P.L.C.

(57) ABSTRACT

A pre-filled syringe is disclosed, comprising a barrel and a plunger, the barrel having an outlet, the barrel containing a pharmaceutically acceptable solution having a non-physiological pH, wherein the syringe further comprises an ion exchange material. The ion exchange material is provided at a position to allow contact with the pharmaceutically acceptable solution upon ejection of the pharmaceutically acceptable solution from the barrel via the outlet. The ion exchange material is capable of adjusting the pH of the solution from a non-physiological pH, at which the pharmaceutically acceptable solution is stored in order to ensure acceptable shelf life, to a more physiological pH at which the discom-
(Continued)

fort and/or pain experienced during injection may be alleviated.

15 Claims, 3 Drawing Sheets

(51) Int. Cl.
   *A61M 5/19* (2006.01)
   *A61M 5/31* (2006.01)
   *A61M 5/32* (2006.01)
(52) U.S. Cl.
   CPC .............. *A61M 5/329* (2013.01); *B01J 47/15* (2017.01); *A61M 2005/3128* (2013.01); *A61M 2205/02* (2013.01); *A61M 2205/19* (2013.01)
(58) Field of Classification Search
   CPC .............. A61M 5/329; A61M 2202/00; A61M 2202/0007; A61M 2202/0028; A61M 2202/0064; A61M 2202/0078; A61M 2205/02; A61M 2205/19; A61M 2205/75; A61M 5/158; A61M 5/1582; A61M 5/32; A61M 5/3286; A61M 5/3293–3298; A61M 2005/1581–1588; A61M 2202/0042; B01J 47/012; B01J 47/018; B01J 47/019; B01J 47/022; B01J 47/024; B01J 47/12; B01J 47/133; B01J 47/15
   See application file for complete search history.

(56) References Cited

U.S. PATENT DOCUMENTS

| | | | |
|---|---|---|---|
| 6,767,460 B1* | 7/2004 | Clough | .................. C02F 1/288 210/502.1 |
| 2003/0225378 A1 | 12/2003 | Wilkie et al. | |
| 2004/0214311 A1* | 10/2004 | Levy | ..................... A61K 45/06 435/287.2 |
| 2013/0115569 A1* | 5/2013 | Lambert | ........... A61M 5/31596 433/90 |
| 2013/0302384 A1* | 11/2013 | Hiraoka | .................. A61K 9/19 604/199 |

FOREIGN PATENT DOCUMENTS

| | | |
|---|---|---|
| JP | 2002538945 A | 11/2002 |
| WO | WO-2000051701 A2 | 9/2000 |
| WO | 2009029795 A1 | 3/2009 |
| WO | 2012102216 A1 | 8/2012 |

OTHER PUBLICATIONS

Written Opinion from PCT Application No. PCT/EP2018/081588 dated Feb. 12, 2019.
Office Action from corresponding Korean Application No. 10-2020-7016235 dated Apr. 17, 2023.

* cited by examiner

SYRINGE ASSEMBLY WITH ION-EXCHANGE MATERIAL

TECHNICAL FIELD

The present invention relates to a pre-filled syringe, in particular a pre-filled syringe comprising an ion exchange material for adjusting the pH of a pharmaceutically acceptable solution; a needle unit, a method for manufacturing a pre-filled syringe; a syringe comprising an ion exchange material for adjusting the pH of a pharmaceutically acceptable solution; a method for parental administration of pharmaceutical solution; a method for preventing, avoiding or reducing pain associated with parental administration of a pharmaceutically acceptable solution; kit of part comprising a pre-filled needle unit; and a kit of parts comprising a syringe and a needle unit.

BACKGROUND

According to the American Autoimmune Related Diseases Association, approximately 50 million people suffer from an autoimmune disease only in the US. An autoimmune disease is defined as a condition arising from an abnormal immune response to a normal body part and can severely impact the life of patients suffering from these conditions.

Several autoimmune diseases, such as rheumatoid arthritis, are typically treated using protein based drugs which are administered subcutaneously. Such drugs typically require administration at least daily. One example of such a drug is Kineret® (anakinra), used in the treatment of rheumatoid arthritis. One common problem associated with subcutaneous administration of such drugs is that the administration can be associated with discomfort, even pain, at the injection site and/or irritation of the skin of the patient. The causes of injection discomfort or pain are numerous and complex. Solution properties such as tonicity, pH, buffer type and buffer strength are known to impact the injection discomfort (e.g. Fransson and Espander-Jansson, 1996; Laursen, 2006). Kineret® (anakinra for injection) is formulated at 150 mg/ml with a 10 mM sodium citrate buffer (pH 6-7) and sodium chloride (140 mM) as tonicity agent. The choice of pH range was driven by finding the optimal stability of anakinra during long term storage. The human body fluids typically have a pH around 7.4 and injection of solutions having a lower, non-physiological pH may cause discomfort and even pain in the patient.

Injection of a solution having a higher, non-physiological pH may likewise cause discomfort or pain.

Thus, there exists a need in the art today for treatments which avoid or reduce the pain associated with injection of drugs.

SUMMARY

It is an object of the present invention to provide injection instruments that are useful for alleviating some of the problems of the prior art.

According to the present disclosure, this and other objects are met by the invention as defined in the different aspects herein.

Hence, according to a first aspect, there is provided a pre-filled syringe comprising a barrel and a plunger, the barrel having an outlet where a solution can be ejected from the barrel, the barrel containing a pharmaceutically acceptable solution having a non-physiological pH. The syringe further comprises an ion exchange material provided such that the pharmaceutically acceptable solution, when contained within the barrel, does not contact the ion exchange material, wherein the ion exchange material is provided at a position to allow contact with the pharmaceutically acceptable solution upon ejection of the pharmaceutically acceptable solution from the barrel via the outlet.

The present invention is based on the realization that by using a pre-filled syringe with an ion exchange material, the discomfort/and or pain experienced by a patient during injection of a pharmaceutically acceptable solution having a non-physiological pH can be reduced or even eliminated. The ion exchange material is capable of adjusting the pH of the solution from a first non-physiological pH, at which the pharmaceutically acceptable solution is stored in order to ensure acceptable shelf life, to a second more physiological pH at which the discomfort and/or pain experienced during injection is at least alleviated. The non-physiological pH is in the range of 3-6.6 and/or the second pH is in the range of 6.6-8.0.

As used herein, "pre-filled syringe" is understood to mean a syringe, with or without an injection needle, with a drug or a pharmaceutically acceptable solution, optionally containing a drug or active ingredient, contained within the barrel. The pre-filled syringe according to the invention comprises a barrel for containing the solution to be injected into the patient, and a plunger for ejecting the solution to be injected through an outlet. The syringe optionally comprises an injection needle in fluid connection with the outlet. The injection needle may be inserted into the body of a patient in order to allow for e.g. subcutaneous, intramuscular or intravenous administration of the drug or pharmaceutically acceptable solution. Where the pre-filled syringe does not comprise a needle, the barrel may comprise a connection to which a needle may be connected. Such connections are known to a person skilled in the art.

Herein, the term "pharmaceutically acceptable solution" denotes a solution which can be injected into the body for pharmaceutical purposes. It may refer to a pharmaceutical solution. The pharmaceutically acceptable solution may comprise a drug, such as a protein drug or a peptide drug and optionally a buffer solution, such as a citrate buffer. The pharmaceutically acceptable solution may further comprise adjuvants commonly used within the field of pharmaceutical solutions. Such adjuvants are known to the person skilled in the art.

In some examples, the syringe optionally further comprises an injection needle in fluid communication with said outlet. The term "injection needle" as used herein is supposed to be understood as any needle suitable for use in the injection or infusion of drugs into the tissue of a patient. Such needles are known to the skilled person in the art.

A "non-physiological pH" is according to the present invention understood as a pH outside of the pH range most common within the human body. A physiological pH is generally denoted as a pH around 7.4, such as in the range of 7.0-7.8. Some pharmaceutically acceptable solutions, such as protein drugs or peptide containing solutions often comprise a buffer which provides the pharmaceutically acceptable solution a non-physiological pH, typically an acidic pH, in order to increase the shelf life solution or drug as such. The pharmaceutically acceptable solution is typically an aqueous solution. Kineret® (anakinra) is one such drug. Kineret® is provided in a citrate buffer having an acidic pH in order to increase its shelf-life. Injecting an acidic solution into a patient is typically associated with pain and/or discomfort in the patient.

An "ion exchange material" according to the present invention is a material capable of exchanging ions with the pharmaceutically acceptable solution. Preferably, the ion exchange material is capable of exchanging positive ions for $H^+$ with the pharmaceutically acceptable solution in order to raise the pH of the solution upon contact with the ion exchange material. For instance, the ion exchange material may be capable of exchanging hydronium or hydrogen ions from the solution to other positive ions, such as sodium ions or calcium ions, from the ion exchange material in order to raise the pH of the pharmaceutically acceptable solution. The ion exchange material is typically a porous solid material, such as a porous organic or inorganic material, for instance a zeolite. In particular, the present inventor found that zeolite materials having $Ca^{2+}$, $Na^+$ or $H^+$ as counter-ions could produce a desirable pH shift of a pharmaceutically acceptable solution.

The ion exchange material is provided in the syringe at a location such that it does not contact the pharmaceutically acceptable solution until just prior to injection. The ion exchange material is provided at a position to allow contact with the pharmaceutically acceptable solution upon ejection of the pharmaceutically acceptable solution from the barrel via the outlet, that is at a position such that when an operator of the syringe (e.g. patient or a medically trained staff) presses the plunger down the barrel to eject the solution, the pharmaceutically acceptable solution contacts the ion exchange material before being ejected from the syringe. In some examples, the ion exchange material is provided at a position along an ejection path from the barrel.

The pharmaceutically acceptable solution is preferably provided in the syringe at the upstream side of the ion exchange material. The ion exchange material should be capable of adjusting the pH during the time it takes for the operator to eject the solution from the syringe, which is typically in the range of 10-120 seconds, such as in the range of 15-100 seconds, for example in the range of 20-60 seconds.

The term "contact" is intended to denote a physical contact between the ion exchange material and the solution. Preferably, the ion exchange material is a porous material. Thus, for example, it allows the pharmaceutically acceptable solution to flow through the porous material, thus providing contact between the pharmaceutically acceptable solution and the ion exchange material when the solution flows through the porous ion exchange material. In some examples, the contact may also be provided in that the pharmaceutically acceptable solution flows beside the ion exchange material in a manner such that there is provided physical contact between the pharmaceutically acceptable solution and the ion exchange material.

An advantage of the present invention is that by adjusting the pH to a physiological pH just prior to injection into the patient, the advantages obtained by storing the solution at a non-physiological pH and injecting it into the patient at a physiological pH can be combined. As such, a means for administration is provided which allows both for storing the pharmaceutically acceptable solution within the syringe, or in a separate container for later filling of the syringe, at a low pH in order to increase the shelf-life of the pharmaceutically acceptable solution and for injecting the pharmaceutically acceptable at an adjusted pH at which the discomfort/pain associated with injection of a solution having a non-physiological pH can be alleviated. Thus, a pre-filled syringe according to the present disclosure can be stored before use without degradation of the pharmaceutically acceptable solution.

The pre-filled syringe can be stored, without significant degradation of the contained pharmaceutical product, at a temperature of 2-30° C., such as of about 2-15° C., for example at a temperature of about 2-8° C., for a time period of at least one week; two weeks; three weeks; four weeks; five weeks; six weeks; eight weeks, 16 weeks, 20 weeks, 25 weeks, 30 weeks, 35 weeks, 40 weeks, 45 weeks, one month, two months, three months, four months, five months, six months, seven months, eight months, or more, such as 1 to 5 years. The pre-filled syringe can also be stored, without significant degradation of the contained pharmaceutical product, at a temperature of above 10° C., e.g. at 10-30° C., for instance at 15-30° C., for a time period of at least one week; two weeks; three weeks; four weeks; five weeks; six weeks; eight weeks, 16 weeks, 20 weeks, 25 weeks, 30 weeks, 35 weeks, 40 weeks, 45 weeks, one month, two months, three months, four months, five months, six months, seven months, eight months, or more, such as 1 to 5 years or 2 to 5 years.

In embodiments of the present invention, the ion exchange material is adapted to, upon contact with the solution, adjust the pH of the solution from a first, acidic pH to a second pH, wherein the second pH is higher than the first pH. The first pH is typically acidic in order to provide the pharmaceutically acceptable solution with a longer shelf-life. The second pH may preferably be a physiological pH, or at least a pH at which the pain associated with injection of the non-physiological solution is at least alleviated.

In embodiments, the second pH is at least 6.6, such as at least 6.7, preferably at least 6.8, more preferably at least 6.9. By adjusting the pH of the solution to a higher pH closer to the physiological pH of the human body, the discomfort and/or pain experienced by the patient can be alleviated.

In embodiments, the first, non-physiological pH is in the range of 3-6.6 and/or the second pH is in the range of 6.6-8.0, such as in the range of 7.0-8.0, preferably 7.1-8.0. In an example, when the pharmaceutically acceptable solution is Kineret®, the first pH may be 6.5, and the second pH is at least 6.6, or at least 7.0, such as in the range of 7.0-8.0, or 7.1-8.0. At the higher, more physiological pH, the pain associated with injection of a solution having a low pH is alleviated.

In some embodiments, the ion exchange material is provided at a position along an ejection path from the barrel. Preferably, the ion exchange material is provided along the ejection path adjacent to the outlet of the barrel. The ejection path is defined as the path the pharmaceutically acceptable solution takes during ejection from the barrel. If the ion exchange material is provided in the ejection path, the solution necessarily contacts the ion exchange material during ejection from the syringe via the outlet. The ion exchange material is preferably provided along the ejection path such that it does not contact the solution until the plunger is pressed down the barrel.

One way to ensure that the solution does not contact the ion exchange material prematurely, that is before the operator presses the plunger down the barrel, is to provide a separator at a position between the pharmaceutically acceptable solution and the ion exchange material.

In embodiments, the pre-filled syringe comprises a separator arranged at a position along an ejection path from the barrel, and the pharmaceutically acceptable solution is present upstream of said separator along said ejection path, and the ion exchange material is provided downstream of the separator along said ejection path. The separator in a first state prevents the pharmaceutically acceptable solution from contacting the ion exchange material, and in a second state allows fluid communication between the pharmaceutically acceptable solution and the ion exchange material, such as to allow contact therebetween. The separator should be configured such that substantially no solution can pass the separator until the operator deactivates the separator e.g. by pressing the plunger down the barrel. The separator may preferably enter the second state when the plunger is being pressed down the barrel. The plunger will then compress the solution so that it exerts a pressure on the separator. When the pressure reaches a critical level, the separator will enter the second state and allow the solution to pass and contact the ion exchange material such that the pH can be adjusted and the solution ejected from the syringe. One example of a separator is a pressure-responsive membrane, such as a super-hydrophobic membrane or a collapsible membrane. Other mechanisms may also be contemplated, such as a valve, preferably a ball valve, which can be operated from the outside of the barrel. The operator of the pre-filled syringe may thus open the valve just prior to injection. In some examples, the valve is a pressure-responsive valve which provides fluid communication between the pharmaceutically acceptable solution and the ion exchange material only after a certain pressure threshold value has been obtained.

In embodiments, the separator is selected from the group consisting of a collapsible, liquid impermeable membrane, a super-hydrophobic material, a valve, a damper and an air pocket. A collapsible, liquid impermeable membrane may have a first state in which it is impermeable to the solution and a second state, in which the membrane is collapsed, liquid impermeable membrane collapses, which allows the pharmaceutically acceptable solution to be in fluid connection with the ion exchange material. The collapse of the collapsible, liquid impermeable membrane can be introduced by an increased pressure acting on the membrane due to actuation of the plunger in the barrel. When the membrane is subject to a threshold pressure, it collapses.

Super-hydrophobic materials may be impermeable to aqueous liquids until subjected to a threshold pressure, at which point aqueous liquids may penetrate the membrane to allow physical contact between the pharmaceutically acceptable solution and the ion exchange material provided on the other side of the membrane.

Dampers and valves are known to a person skilled in the art. The dampers and valves may be operated by an operator from the outside of the syringe.

An air pocket may be contained within a bag, or balloon, which conforms to the inner shape of the barrel. When the pressure from the pharmaceutically acceptable solution reaches a threshold value, the bag or balloon breaks and the solution is allowed to be in fluid connection with the pharmaceutically acceptable solution.

In some embodiments, the ion exchange material is provided in the barrel between the pharmaceutically acceptable solution and the outlet. The ion exchange material may preferably have the shape of a cylinder or disc, for use in syringes of circular cross-section. The diameter of the cylinder or disc is typically chosen so that the cylinder or disc conforms to the inner periphery of the barrel. Preferably, the dimensions, including diameter, of the cylinder or disc may be chosen such that substantially all of the pharmaceutically acceptable solution passes through the ion exchange material during ejection of the pharmaceutically acceptable solution from the syringe. The height of the cylinder may be less than 15 mm, such as less than 10 mm, such as in the range of 3-10 mm.

The term "cylinder" is supposed to denote also substantially cylindrical objects.

In some embodiments, the syringe comprises an injection needle mounted in fluid communication with said outlet.

In embodiments disclosed herein, the ion exchange material is contained within said needle. The ion exchange material may have shape such that it conforms to the inner shape of the needle. The ion exchange material may be sintered to achieve and/or maintain this shape. Preferably, the ion exchange material may be spark plasma sintered.

In some examples, ion exchange material is contained in a female luer cone cannula hub. The ion exchange material may have shape such that it conforms to the inner shape of the female luer cannula hub.

In some embodiments, the ion exchange material comprises a zeolite material. A plethora of zeolite materials capable of acting as ion exchange materials are known to the skilled person in the art. The zeolite materials have a microporous pore system. Mesoporous and microporous pore systems may also be contemplated, as well as hierarchical pore systems.

In some embodiments, the zeolite material is an aluminosilicate zeolite material loaded with positive ions, such as $Na^+$, $H^+$ and/or $Ca^{2+}$ having a $SiO_2/Al_2O_3$ molar ratio above 1.5; and/or a $Na_2O$ content below 10 wt-% of the total zeolite weight. Preferably, the aluminosilicate zeolite material may be loaded with $Na^+$ and/or $Ca^{2+}$. Zeolite materials may be loaded with more than one type of counter-ions. In the present disclosure, the zeolite material is preferably loaded with positive ions. The inventors have surprisingly found using a zeolite material loaded the with $Na^+$, $H^+$ and/or $Ca^{2+}$ ions, preferably $Na^+$ and/or $Ca^{2+}$, the pH of the pharmaceutically acceptable solution having a non-physiological pH can be adjusted swiftly to a pH at which the injection causes less pain. The inventors have furthermore found that a $SiO_2/Al_2O_3$ molar ratio above 1, such as above 1.5, preferably in the range of in the range of 1.5-1000, such as 1.5-100, is especially advantageous. Also, a sodium content in the zeolite material of below 15 wt-% of the total zeolite weight, such as below 10 wt-% of the total zeolite weight has been found advantageous in that it provides a swift adjustment of the pH of the pharmaceutically acceptable solution. In particular, the present inventor found that zeolite materials having $Ca^{2+}$, $Na^+$ or $H^+$ as counter-ions could produce a desirable pH shift of a pharmaceutically acceptable solution.

In some embodiments the ion exchange material comprises a mesoporous silica. Mesoporous silica is a mesoporous silicon dioxide. The mesoporous silica may be functionalized, in order to improve its ion exchange properties.

In some embodiments, the ion exchange material comprises a polystyrene material. The polystyrene material may preferably be functionalized such that it is capable of adjusting the pH of a pharmaceutically acceptable solution.

In some embodiments, the ion exchange material comprises a material selected from mesoporous silica and a polystyrene material.

The pharmaceutically acceptable solution may be an aqueous solution.

In some embodiments, the pharmaceutically acceptable solution comprises an acidic buffer solution, such as a citrate buffer. The citrate buffer may lower the pH of the pharmaceutically acceptable solution in order to provide acceptable shelf-life. Several pharmaceutical solutions, such as Kineret®, exhibits a longer shelf-life in acidic environments, as compared to physiological pH.

In some embodiments, the pharmaceutically acceptable solution comprises a protein drug or a peptide drug. Protein drugs should generally be understood as drugs including at least one protein as an active ingredient. Peptide drugs should generally be understood as drugs including at least one peptide as an active ingredient. Protein drugs and peptide drugs are commonly used in the treatment of autoimmune diseases. Protein drugs and peptide drugs may have a short shelf life at a physiological pH. Thus, it is advantageous to store them at a low pH in order to increase their shelf life.

In some embodiments of the invention the protein or peptide drug is an IL-1 receptor antagonist, such as anakinra. IL-1 receptor antagonists, and in particular Kineret® (anakinra) has been shown to be useful in the treatment of autoimmune diseases such as rheumatoid arthritis. Kineret® is provided in a citric acid buffer in order to increase its shelf life. The pH of Kineret® is about 6.5. Thus, subcutaneous injection of Kineret® is generally associated with discomfort and/or pain in the patient. One advantage of the pre-filled syringe of the invention is that it is capable of raising the pH of Kineret® just prior to injection into the patient to alleviate such discomfort and/or pain.

According to a further aspect, there is provided a method for adjusting the pH of a pharmaceutically acceptable solution having a non-physiological pH, comprising the steps of
a) providing a syringe according to the first aspect of the invention comprising the pharmaceutically acceptable solution and an ion exchange material;
b) contacting the pharmaceutically acceptable solution with the ion exchange material, whereby the pH of the solution is increased from the first acidic pH to a second pH.

The inventors have found that by using the method of this aspect of the invention, the pH of a pharmaceutically acceptable solution can be kept at a first pH in the syringe in order to increase the shelf-life of the pre-filled syringe, and by contacting the pharmaceutically acceptable solution with an ion exchange material, the pH of the pharmaceutically acceptable solution can be increased to a second pH. By keeping pharmaceutically acceptable solutions, such as Kineret®, at a low pH during storage their shelf-life can be prolonged several times. However, injecting a pharmaceutically acceptable solution having a low pH into a patient is typically associated with discomfort and/or pain in the patient. The method according to the second aspect of the invention allows for the pH of the solution to be increased to a second pH just prior to injection. The second pH is higher than the first pH and should be closer to the physiological pH than the first pH. Thus, the problems associated with pain and/or discomfort caused by injection of a solution at an acidic pH can be alleviated. At the same time, the benefits of storing the pharmaceutically acceptable solution at a first, acidic pH can be maintained. The step of contacting the pharmaceutically acceptable solution with the ion exchange material may be performed just prior to that the pharmaceutically acceptable solutions is ejected from the syringe. The ion exchange material should be capable of adjusting the pH during the time it takes for an operator to eject the solution from the syringe, which is typically in the range of 10-120 seconds, such as in the range of 15-100 seconds, for example in the range of 20-60 seconds. In some instances, it may take 5-15 seconds.

The syringe used to perform this method is the syringe disclosed in the first aspect of the invention. The syringe may be defined by any one of the embodiments disclosed therein.

In some embodiments of the present invention, the step b) further comprises pressing the plunger down the barrel of the syringe. By pressing the plunger down the barrel, the pharmaceutically acceptable solution will come into contact with the ion exchange material. The step b) may be performed by the patient himself/herself or another operator, such as a physician or a parent.

In embodiments of the present invention, the method comprises a further step of c) ejecting the pharmaceutically acceptable solution from the syringe. Pressing the barrel down the plunger will cause the pharmaceutically acceptable solution to be pushed towards the syringe outlet so that it is ejected from the syringe.

In a further aspect, there is provided a method for parental administration of a pharmaceutically acceptable solution to a patient in need thereof, wherein the method comprises the steps of
a) providing a syringe according to the invention comprising the pharmaceutically acceptable solution and an ion exchange material;
b) contacting the solution with the ion exchange material, e.g. by pressing the plunger down the barrel, whereby the pH of the solution is increased from a first, non-physiological pH to a second pH;
c) injecting or infusing the solution into the patient.

In some examples, the step b) comprises contacting the ion exchange material with the solution.

The method provides several advantages. Firstly, it allows for an increase in the pH of the pharmacologically acceptable solution from a non-physiological pH to a second, physiological pH prior to injection or infusion into the patient such that the discomfort and/or pain associated with the injection of pharmaceutically acceptable solutions having a non-physiological pH can be alleviated. Secondly, it allows for pharmaceutically acceptable solutions to be stored at a non-physiological pH in order to increase the shelf-life of the solution.

The term "parental administration" is known to a person skilled in the art. Preferably, the parental administration is a subcutaneous injection. The parental administration may also be intramuscular or intravenous.

The method is preferably performed by a patient himself/herself or by a physician or other medically trained persons. The method may be particularly advantageous when performed by the patient, as it facilitates self-administration by alleviating the discomfort typically experienced when injecting solutions having a non-physiological pH into the body. Less discomfort may make the patient less prompted to interrupt administration or even cancel the treatment.

The terms "injecting" and "infusion", may in the present disclosure be used interchangeably. Both are intended to denote the introduction of a pharmaceutically acceptable solution into the body of the patient.

In another aspect, there is provided a method for preventing, avoiding or reducing pain associated with parental administration of a pharmaceutically acceptable solution comprising a buffer having a non-physiological pH in a patient, wherein the method comprises the steps of
a) providing a syringe according to any one of the claims 1 to 18 comprising the pharmaceutically acceptable solution and an ion exchange material;
b) contacting the solution with the ion exchange material, by pressing the plunger down the barrel, whereby the pH of the solution is increased from a non-physiological pH to a second pH;
c) injecting or infusing the solution into the patient.

In a still further aspect, there is provided a method for manufacturing a pre-filled syringe according to the invention comprising steps of:
a) providing a syringe having a plunger and a barrel, the barrel having an interior volume;
b) providing the syringe with an ion exchange material at a position that is not in fluid communication with the interior volume of the barrel;
c) placing a pharmaceutically acceptable solution within said barrel.

Syringes comprising a plunger and a barrel are known to the person skilled in the art. The syringe may further comprise an outlet, and optionally a needle. The step of providing the syringe with an ion exchange material at a position that is not in fluid communication with the interior volume of the barrel can be accomplished in a number of ways. In one example, it may be accomplished by providing the ion exchange material within the barrel of the syringe near the outlet of the syringe, and to place a separator within the barrel upstream of the ion exchange material. The ion exchange material may have a shape such that it conforms to the inner shape of the syringe and may form a plug that fills at least a substantial part of the cross-sectional area of the barrel. Preferably, the ion exchange material has a substantially cylindrical shape. Furthermore, the separator is placed such that it prevents fluid from contacting the ion exchanger material before the plunger has been pressed down the barrel. The separator typically has a shape such that it conforms to the inner shape of the barrel and forms a plug that fills a cross-sectional area of the barrel to form two compartments sealed from one another by the separator. Preferably, during production, the ion exchange material is arranged within the barrel before the separator is positioned to seal the ion exchange material form the compartment or part of the barrel intended to contain the pharmaceutically acceptable solution. Both the step of arranging the ion exchange material within the syringe and the step of arranging the separator within the syringe may be performed by conventional means known to a person skilled in the art, manually or in an automated process.

A pharmaceutically acceptable solution is subsequently placed within the barrel upstream the ion exchange material and, if a separator has been provided, upstream the separator. The pharmaceutically acceptable solution is placed such that it does not contact the ion exchange material until an operator of the pre-filled syringe presses the plunger down the barrel.

In some embodiments, the ion exchange material is contained within a needle unit, and the step b) involves connecting said needle unit to the barrel. Preferably, the ion exchange material has a shape such that it conforms to the inner shape of the needle unit. The ion exchange material may be placed within the needle by means known to a person skilled in the art, such as manual means or automatic means.

In embodiments, the ion exchange material is a particulate zeolite material and wherein step b) comprises b-i) sintering the zeolite material to a shape such that it matches to the inner shape of a needle of the needle unit and b-ii) placing the sintered zeolite material in the needle. Sintering zeolites materials to a specific shape is known to a person skilled in the art.

In some embodiments, the ion exchange material is a particulate zeolite material and wherein step b) comprises b-1) sintering a zeolite material to a shape such that it conforms to the inner shape of the barrel and b-ii) placing the sintered zeolite material in the barrel.

That the shape of the sintered zeolite material "conforms to" the inner shape of the barrel and/or needle is intended to denote that the shape of the sintered zeolite material matches the inner shape of the barrel and/or needle such that it can be positioned therein and act as an ion exchange material such as disclosed herein.

In some embodiments of the present invention, the method further comprises the step of b1) providing a separator in the barrel. The separator may preferably be a separator such as the separators disclosed above in relation to the first aspect of the invention.

In a further aspect, there is provided a syringe comprising a barrel and a plunger, the barrel having an interior volume adapted to contain a pharmaceutically acceptable solution having a non-physiological pH, wherein the syringe further comprises an ion exchange material provided within the syringe such that it is not in fluid communication with the interior volume of the barrel adapted to contain the pharmaceutically acceptable solution, and wherein the ion exchange material is provided at a position to, in use, allow contact with the pharmaceutically acceptable solution upon ejection of the pharmaceutically acceptable solution from the barrel.

The inventors have realized that by providing a syringe comprising an ion exchange material such that it is not in fluid communication with the interior volume of the barrel, and wherein the ion exchange material is provided at a position to allow contact with the pharmaceutically acceptable solution upon ejection of the pharmaceutically acceptable solution from the barrel, the syringe can be used to adjust the pH of a pharmaceutically acceptable solution from a first, non-physiological pH to a second, physiological pH, as described above. The first pH is in the range of 3-6.6 and/or the second pH is in the range of 6.6-8.0.

The syringe is adapted to accommodate a pharmaceutically acceptable solution within its barrel. Before using the syringe to inject a solution into a patient, the patient or a physician operating the syringe fills the barrel with the pharmaceutically acceptable solution upstream the ion exchange material.

When the plunger is pressed down the barrel, the pharmaceutically acceptable solution is forced downstream the barrel such that it contacts the ion exchange material. Upon contact with the ion exchange material, the pH of the solution may be adjusted from a first non-physiological pH to a second, physiological pH.

In embodiments, the syringe further comprises a separator as described herein.

In some embodiments, the syringe further comprises an injection needle mounted in fluid communication with an outlet of the barrel. The injection needle may be any needle adapted for use in injection of a pharmaceutically acceptable solution into the patient, e.g. by penetrating the skin tissue. Such needles are known to a person skilled in the art. In some examples, the ion exchange material is provided within the needle.

In some embodiments, the ion exchange material is adapted to, upon contact with the pharmaceutically acceptable solution, adjust the pH of the solution as described herein.

In embodiments, the pharmaceutically acceptable solution is the pharmaceutically acceptable solution as described herein.

In a further aspect of the invention, there is provided a kit comprising:

i) a pre-filled syringe comprising a barrel and a plunger, the barrel having an outlet and containing a pharmaceutically acceptable solution having a non-physiological pH; and ii) a needle unit comprising an injection needle and an ion exchange material, wherein the needle unit is adapted to be mounted on the pre-filled syringe to be in fluid connection with said outlet and to allow ejection of the pharmaceutically acceptable solution via the needle, and the ion exchange material is arranged to be contacted by the pharmaceutically acceptable solution upon ejection of the pharmaceutically acceptable solution via the needle.

The kit may be provided in parts and assembled by the operator just prior to injection, by attaching the needle unit to the pre-filled syringe. When the kit is adapted to be assembled just prior to injection, the pre-filled syringe requires no separator in order to prevent the pharmaceutically acceptable solution prematurely. As soon as the needle unit has been mounted on the syringe the syringe is ready to be used to inject the pharmaceutically acceptable solution contained therein. The kit may preferably be assembled by the patient or a physician. The needle unit may preferably be mounted to the syringe by a connection at the outlet of the barrel and could be any connection known to a person skilled in the art, such as a bayonet mount or a thread screw mount.

However, in some embodiments, the pre-filled syringe may further comprise a separator such as the separator as described herein.

In some embodiments the ion exchange material is adapted to, upon contact with the pharmaceutically acceptable solution, adjust the pH of the solution as described herein.

In some embodiments, the pharmaceutically acceptable solution is as described herein.

In yet another aspect, there is provided a kit comprising:
i) a syringe comprising a barrel and a plunger, the barrel having an interior volume adapted to contain a pharmaceutically acceptable solution having a non-physiological pH;
ii) a needle unit as defined herein.

In some embodiments, the pre-filled syringe comprises a separator as defined herein.

In a still further aspect, there is provided a needle unit comprising an injection needle and an ion exchange material, wherein the ion exchange material is contained within the injection needle.

The needle unit is preferably adapted to be mounted in fluid communication with a syringe, and the needle unit further comprising an injection needle adapted for injection of a pharmaceutically acceptable solution into the body of a human or animal, and an ion exchange material, wherein the ion exchange material is contained in the needle.

The needle unit is preferably adapted to be mounted on a pre-filled syringe. The ion exchange material is preferably contained within the injection needle such that it conforms to the inner shape of the needle and fills a cross-sectional area of the needle.

In some embodiments, the ion exchange material may be adapted to, upon contact with a pharmaceutically acceptable solution, adjust the pH as described herein.

In some embodiments, the ion exchange material may be a zeolite material as described herein.

It is noted that the invention relates to all possible combinations of features recited in the claims.

The above described and other features are exemplified by the following figures and detailed description.

BRIEF DESCRIPTION OF APPENDED DRAWINGS

The invention will hereinafter be described in detail by reference to exemplary embodiments as illustrated in the following drawings, in which.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person. As illustrated in the figures, the sizes of layers and regions may be exaggerated for illustrative purposes and, thus, are provided to illustrate the general structures of embodiments of the present invention. Like elements are numbered alike.

Figure 1A:
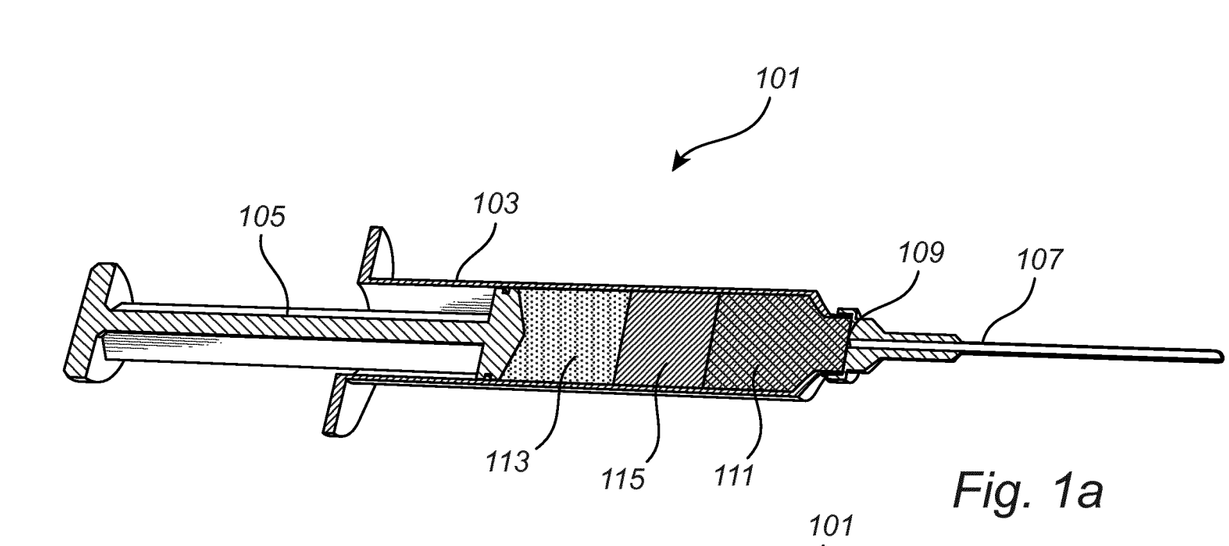
FIGS. 1a-1b each schematically shows a pre-filled syringe according to embodiments of the invention.
Figure 1B:
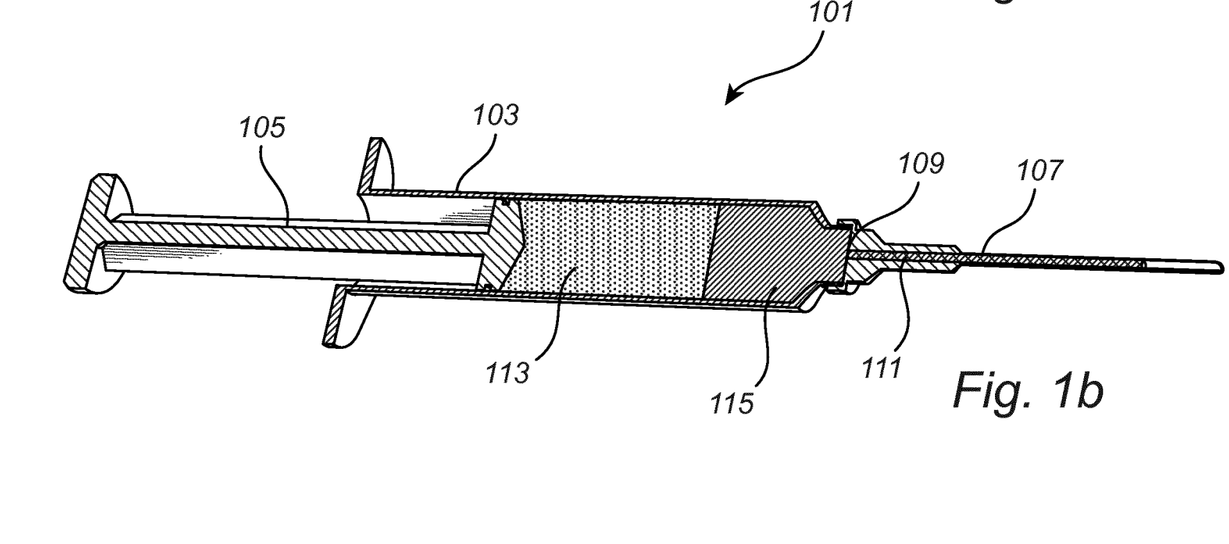

FIGS. 1a to 1b are schematic illustrations of different conceivable embodiments of a pre-filled syringe 101 according to embodiments of the invention. In FIG. 1a the pre-filled syringe 101 is depicted as having a substantially cylindrical barrel 103 and a plunger 105. The pre-filled syringe of this embodiment is further provided with an injection needle 107 fixed to an outlet 109 of the barrel 103. In this embodiment, an ion exchange material 111 is contained within the barrel 103, provided in an outlet path between the plunger 105 and the outlet 109 of the barrel 103. In this embodiment the ion exchange material 111 has the shape of a porous cylinder. A pharmaceutically acceptable solution 113 is contained within the barrel 103. A separator 115, e.g. a pressure-responsive separator, is also contained within the barrel 103 between the pharmaceutically acceptable solution 113 and the ion exchange material 111 to prevent the pharmaceutically acceptable solution 113 from contacting the ion exchange material 111 before the plunger 105 is pushed down the barrel 103 to eject the pharmaceutically acceptable solution 111 from the syringe 101. The ion exchange material 111 is arranged to be retained within the syringe upon ejection of the pharmaceutically acceptable solution.

The ion exchange material 111 is typically provided downstream the separator 115 within the barrel. The ion exchange material 111 and the separator 115 may be adjacent to each other. The ion exchange material 111 may have a larger mass than the separator 115. The separator 115 may be of any shape and form, provided that it prevents contact between the pharmaceutically acceptable solution and the ion exchange material prematurely, e.g. until the plunger 105 is being pressed down the barrel 103 and/or the separator is deactivated, at which point it allows the pharmaceutically acceptable solution 113 to contact the ion exchange material 111.

In embodiments, the pre-filled syringe 101 may not comprise an injection needle 107. Instead, the pre-filled syringe 101 may be adapted to be connected to an injection needle provided separately. The connection is preferably provided at the outlet 109, and could be any connection known to a person skilled in the art, such as a bayonet mount or a thread screw mount.

The pharmaceutically acceptable solution 113 contained within the barrel 103 is generally intended for parenteral administration and may have a non-physiological pH, in particular an acidic pH. The solution 113 may have a low pH in order to increase the shelf-life of the solution 113, including any drug or active compound such as a protein drug or peptide drug, contained therein. In use, an operator, which may be a medically trained person or the patient himself/herself, presses the plunger 105 down the barrel 103 to push the pharmaceutically acceptable solution 113 along an ejection path from the barrel 103 to contact the ion exchange material 111. The ion exchange material 111 is chosen by a manufacturer and is capable of to exchange ions with the pharmaceutically acceptable solution 113 to provide an increase or decrease of the pH of the solution, as desired, to adjust the pH of the pharmaceutically acceptable solution 113 to a more physiological pH (i.e. about pH 7). Hence, upon contact with the ion exchange material 111, the non-physiological pH of the pharmaceutically acceptable solution 113 is adjusted towards a more physiological pH, such that upon ejection from the syringe 101 and injection into the patient, the pH of the solution is closer to a physiological pH.

FIG. 1b illustrates an alternative embodiment of the pre-filled syringe 101 depicted as having a substantially cylindrical barrel 103 and plunger 105. The pre-filled syringe 101 is in this embodiment is further provided with an injection needle 107 fixed to an outlet 109 of the barrel 103. In this embodiment, an ion exchange material 111 is contained within the injection needle 107. The ion exchange material may be provided as a material arranged to be retained within the needle upon ejection of the pharmaceutically acceptable solution. The syringe is furthermore provided with a pharmaceutically acceptable solution 113 contained within the barrel 103. The pharmaceutically acceptable solution 113 is hindered from prematurely contacting the ion exchange material 111 in the needle 107 by a separator 115. In this embodiment, it may also be possible to omit the separator.

Syringes comprising a barrel and a plunger are well known to a person skilled in the art. Any type of syringe capable of containing an ion exchange material may be contemplated within the scope of the present invention.

In embodiments, the pharmaceutically acceptable solution does not contact the ion exchange material before the plunger is being pressed downstream in the direction of the ejection path. In order to accomplish this, the syringe may comprise a separator. The separator may have a first state in which it prevents the pharmaceutically acceptable solution from contacting the ion exchange material, and a second, pressurized state where it allows the pharmaceutically acceptable solution to flow through or past the separator and into contact with the ion exchange material. The second, pressurized state can be introduced when the plunger is being pressed downstream to push the pharmaceutically acceptable solution along the ejection path of the barrel. The separator prevents the ion exchange material from adjusting the pH of the pharmaceutically acceptable solution prematurely.

In embodiments, the separator may be a liquid impermeable membrane or a super-hydrophobic membrane, which allows the pharmaceutically acceptable solution to pass through the membrane only after a certain pressure threshold value is exceeded. This state can be introduced by a collapse of the membrane. Other pressure-responsive separator working after the same general principle may also be contemplated, such as an air pocket. An air pocket may be a bag or balloon filled with air. The bag or balloon may conform to the inner shape and fill a cross-sectional area of the barrel and fill a cross-sectional area. After a certain pressure threshold value is obtained, the bag or balloon breaks, allowing the solution to flow past and into contact with the ion exchange material. Also contemplated is a solution where the ion exchange material is coated with a separator material, such as a hydrophobic material, which is impermeable to fluid until a certain pressure threshold value has been obtained. The pressure threshold value is obtained when the plunger is being pressed down the barrel. The separator may also a valve or a damper, which may be controlled from the outside of the syringe.

The ion exchange material should preferably be permeable to the pharmaceutically acceptable solution. The ion exchange material should furthermore be capable of, upon contact, adjusting the pH of the pharmaceutically adjustable solution. The ion exchange material should preferably be capable of adjusting the pH of the pharmaceutically acceptable solution from a first, acidic pH to a second pH, wherein the second pH is higher than the first pH. In embodiments, the second pH is at least 6.6. The first acidic pH may be in the range of 3-6.6 and the second pH is at least 6.6, or at least 7.0, such as in the range of 7.0-8.0, or 7.1-8.0.

In order to achieve the pH adjustment, the ion exchange material may be loaded with positive ions, such as $Na^+$, $H^+$, and/or $Ca^{2+}$, preferably $Na^+$ and/or $Ca^{2+}$. Other positive ions may also be contemplated. Preferably, the positive ions have a valence of +1 or +2. The mechanism for the pH adjustment may typically be ion exchange, which mechanism is known to persons skilled in the art. In brief, ion exchange is based on the principle that $H^+$ ions present in a solution may be exchanged by the ion exchange material for another cation, such as $Na^+$ and/or $Ca^{2+}$, or other ions present in the ion exchange material. Thus, the pH of the solution can be increased. In particular, the present inventor found that zeolite materials having $Ca^{2+}$, $Na^+$ or $H^+$ as counter-ions could produce a desirable pH shift of a pharmaceutically acceptable solution.

The duration of the contact between the pharmaceutically acceptable solution and the ion exchange material may correspond to the time it takes, during normal use, to eject the solution from the syringe using the plunger. Such a contact may be sufficient for adjusting the pH. The duration of a typical injection of Kineret® is in the range of 10-100 seconds such as in the range of 10-80 seconds, preferably 20-60 seconds.

The ion exchange material may be a porous material, such as an inorganic porous material. In some embodiments the ion exchange material may be an aluminosilicate material such as a zeolite.

The zeolite material may typically have a silica/alumina ratio of above 1, such as above 1.5, preferably in the range of 1.5-1000. It may also be in the range of 1.5-800, such as in the range of 1.5-500.

Preferably, the zeolite material has a sodium content below 20 wt-% of the total zeolite weight, such as below 15 wt-%, preferably below 10 wt-%.

The zeolite material may in embodiments of the invention be a microporous zeolite. The term microporous is supposed to indicate that the pore diameters in the zeolite material is less than 2 nm. Other pore systems may also be contemplated, such as mesoporous (pore diameter between 2 nm and 50 nm) and macroporous (pore diameter larger than 50 nm).

A number of different zeolites may be contemplated, such as the zeolites marketed under the names Zeoflair, faujasite and Zeolite Y.

Other ion exchange materials may also be contemplated, such as mesoporous silica. The mesoporous silica may optionally be functionalized to improve the ion exchange properties.

The ion exchange material may comprise a polymer, such as a polystyrene material. The polystyrene material may be acidic, such as strongly acidic typically comprising sulfonic acid groups, e.g. sodium polystyrene sulfonate or polyAMPS. The polystyrene material may also be weakly acidic, typically comprising carboxylic acid groups.

In some examples, basic polystyrenes may also be contemplated. The basic polystyrenes may be strongly basic polystyrenes such as polystyrenes comprising quaternary amino groups, for example, trimethylammonium groups, e.g. polyAPTAC). The polystyrenes may also be weakly basic, typically comprising featuring primary, secondary, and/or tertiary amino groups, e.g. polyethylene amine groups.

In embodiments where the ion exchange material is contained in the barrel of the syringe, the ion exchange material may have the shape of a cylinder, such as in the shape of a plug. The diameter of the cylinder is typically chosen so that the plug conforms to inner periphery of the barrel, and fills a cross-sectional area of the barrel. Preferably, the dimensions, including diameter, of the cylinder may be chosen such that substantially all of the pharmaceutically acceptable solution passes through the ion exchange material during ejection of the pharmaceutically acceptable solution from the syringe. The height of the cylinder may be less than 15 mm, such as less than 10 mm, such as in the range of 3-10 mm. The height of the cylinder is preferably roughly proportional to the volume of the pharmaceutically acceptable solution in the syringe. A larger volume of pharmaceutically acceptable solution may require a cylinder having a greater height.

The ion exchange material cylinder may be manufactured by for example sintering, such as spark plasma sintering. Other sintering techniques known to a skilled person in the art are also contemplated.

The ion exchange material may be contained in a porous polymer matrix such polyvinylidene fluoride (PVDF).

The pharmaceutically acceptable solution of the present invention may comprise an acidic buffer, such as a citrate buffer. A reason for using an acidic buffer is that an acidic pH may improve stability of the solution, in particular of a pharmaceutically active agent contained in the solution, which is useful in that it increases the shelf-life. During administration, and in particular subcutaneous administration, pharmaceutically acceptable solutions comprising an acidic buffer may cause irritation and pain. By adjusting the pH of the solution just prior to injection, the pain and/or irritation experienced by patient can be drastically reduced. However, since the stability of the solution is often dependent on that it is provided in a buffered solution with a non-physiological pH, it is important that the pH of the solution is not adjusted prematurely. FIGS. 1a and 1b show two examples of how the solution can be prevented from prematurely contacting the ion exchange material.

The pharmaceutically acceptable solution may comprise a biological drug, such as a protein drug or a peptide drug. In some embodiments, the protein drug may be an IL-1 receptor antagonist (IL-1ra), such as anakinra. Anakinra is a drug used in the treatment of rheumatoid arthritis and requires daily subcutaneous administration. Anakinra may be provided in an acidic buffer in order to increase the stability of the solution so that the shelf-life may be increased. However, it is also contemplated that the drug contained in the pharmaceutically acceptable solution according to embodiments of the present invention may be a non-protein drug, such as a small organic molecule, such as a steroid. Hence, the type of drug or pharmaceutically active agent intended for use with the syringe described herein is not particularly limited, except in that it can be formulated as a liquid composition suitable for parenteral administration and that it benefits (e.g. with regard to stability of shelf life) from a non-physiological pH in solution.

Accordingly, the syringe of the invention may be intended to be used with any injectable pharmaceutical solution having a non-physiological pH.

A pre-filled syringe according to the invention may be manufactured by providing a syringe having a barrel and a plunger with an ion exchange material at a position in the barrel and placing a pharmaceutically acceptable solution within said barrel. The ion exchange material is preferably placed in the syringe before the ion exchange material. Preferably, the ion exchange material is placed in the syringe, followed by a sterilization of the syringe before the barrel is filled with the pharmaceutically acceptable solution. The ion exchange material should be placed downstream from the pharmaceutically acceptable solution.

Arranging the ion exchange material within the injection needle is also contemplated. The ion exchange material may be provided in the syringe an any manner such that the pharmaceutically acceptable solution contacts the ion exchange material before the solution is ejected from the syringe. Preferably, the ion exchange material is sintered to a shape which conforms to the inner shape of the needle.

Figure 2A:
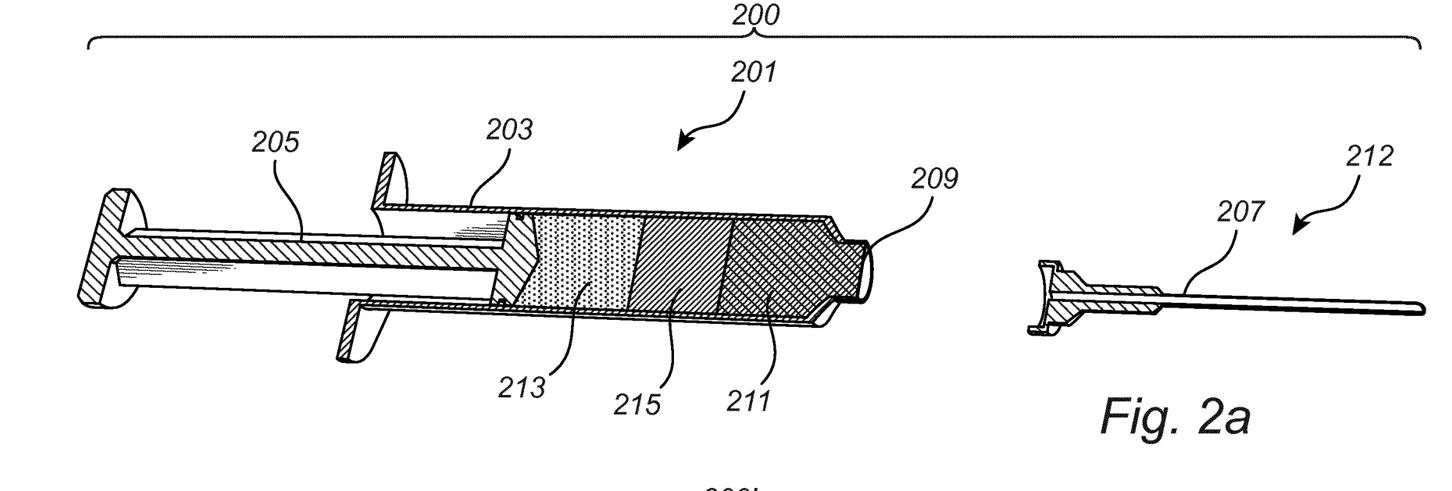
FIGS. 2a-b each schematically shows an assembly comprising a syringe according to embodiments of the invention.

FIG. 2a is a schematic illustration of a kit according to the invention. The kit 200 comprises a pre-filled syringe 201 and a needle unit 212 (also referred to as "injection needle unit"). The pre-filled syringe 201 comprises a barrel 203 and a plunger 205. In the barrel 203, a pharmaceutically acceptable solution 213 is contained. Downstream of the pharmaceutically acceptable solution there is provided an ion exchange material. The barrel 203 further comprises an outlet 209 adapted to allow ejection of the pharmaceutically acceptable solution 213. The outlet 209 is preferably provided with a connection which allows mounting of the needle unit 212 to the outlet 209. The barrel 203 furthermore contains a separator 215 between pharmaceutically acceptable solution 213 and the ion exchange material 211.

The needle unit 212 comprises an injection needle 207. The needle unit 212 is adapted to be mounted on the pre-filled syringe 201, preferably to a connection at the outlet 209 of the barrel. Such connections are known to a person skilled in the art, and comprises thread-screw mounts and bayonet mounts. The connection should allow for fluid connection between the barrel 203 and the needle unit 212.

Figure 2B:
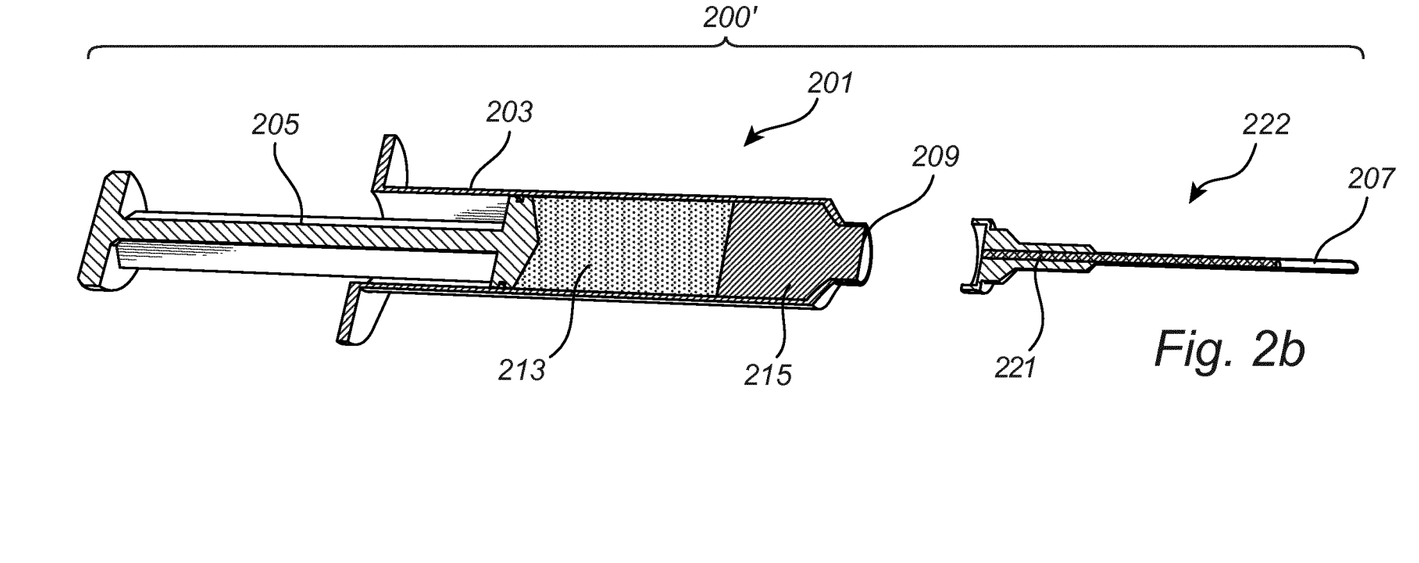

FIG. 2b is a schematic illustration of a kit according to the invention. The kit 200' comprises a pre-filled syringe 201 and a needle unit 222, (also referred to as "injection needle unit"). The pre-filled syringe comprises a barrel 203 and a plunger 205. In the barrel 203, a pharmaceutically acceptable solution 213 is contained. The barrel 203 further comprises an outlet 209 adapted to allow ejection of the pharmaceutically acceptable solution 213. The outlet 209 is preferably provided with a connection which allows mounting of the needle unit 222 to the outlet 209. The barrel 203 furthermore contains a separator 215 between the outlet 209 and the pharmaceutically acceptable solution 213.

The needle unit 222 of FIG. 2b comprises an injection needle 207 and an ion exchange material 221. The needle unit 222 is adapted to be mounted on the pre-filled syringe 201, preferably to a connection at the outlet of the barrel. Such connections are known to a person skilled in the art, and comprises thread-screw mounts and bayonet mounts. The connection should allow for fluid connection between the barrel 203 and the needle unit 222. The ion exchange material 221 is preferably contained within the needle 207 to provide contact between the pharmaceutically acceptable solution 213 and the ion exchange material 221 upon ejection of the pharmaceutically acceptable solution 213 upon ejection via the needle 207. The ion exchange material 221 should be capable of adjusting the pH of a pharmaceutically acceptable solution 213 from a non-physiological pH to physiological pH upon contact between the ion exchange material 221 and the pharmaceutically acceptable solution 213.

The pre-filled syringe and injection needle unit may optionally comprise the elements discussed in relation to FIGS. 1a and 1b.

Figure 3A:
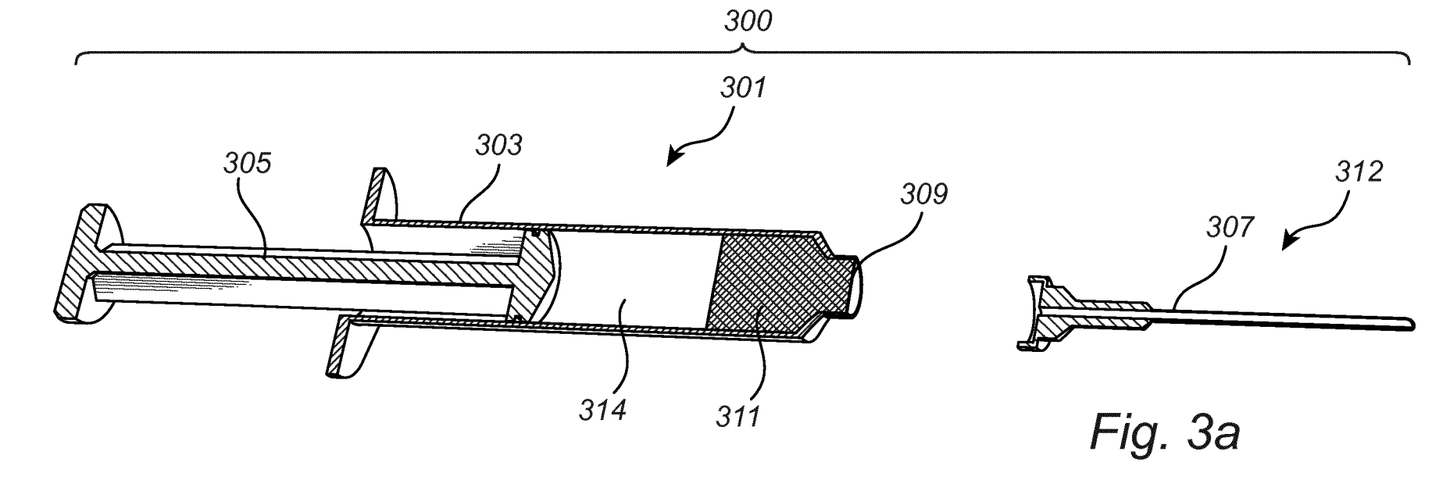
FIGS. 3a-b each schematically shows an assembly comprising a syringe according to other embodiments of the invention.

FIG. 3a schematically shows yet another kit according to embodiments of the invention. The kit 300 comprises a syringe 301 and an injection needle unit 312. The syringe comprises a barrel 303 comprising an interior volume 314 adapted to contain a pharmaceutically acceptable solution and a plunger 305. In the barrel, there is provided a ion exchange material 311. The barrel 303 further comprises an outlet 309 adapted to allow ejection of the pharmaceutically acceptable solution. The outlet 309 is preferably provided with a connection which allows mounting of the needle unit 312 to the outlet 309.

The injection needle unit 312 comprises a needle 307. The needle unit 307 is adapted to be mounted on the syringe 301, preferably to a connection at the outlet 309 of the barrel. Such connections are known to a person skilled in the art, and comprises thread-screw mounts and bayonet mounts. The connection should allow for fluid connection between the barrel 303 and the needle unit 307.

The kit is adapted to be assembled, i.e. by connecting the injection needle unit 312 to the syringe 301 and to be provided with a pharmaceutically acceptable solution in the barrel 303 just prior to injection of the pharmaceutically acceptable solution.

Figure 3B:
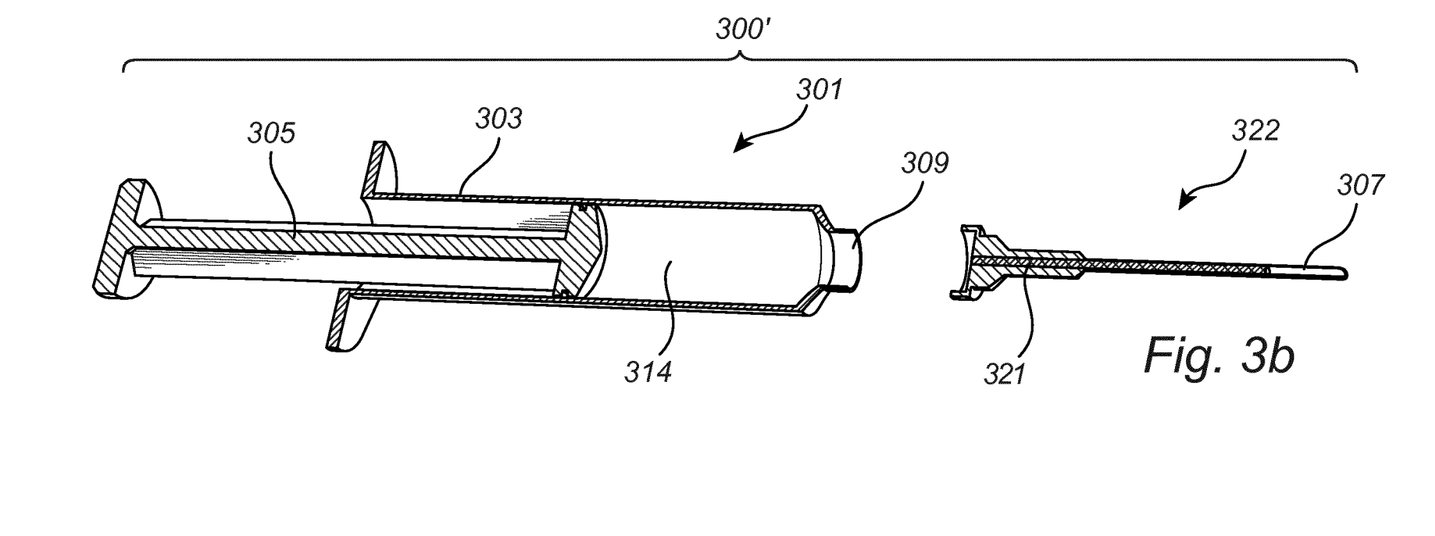

FIG. 3b schematically shows another kit according to embodiments of the invention. The kit 300' comprises a syringe 301 and an injection needle unit 322. The syringe comprises a barrel 303 comprising an interior volume 314 adapted to contain a pharmaceutically acceptable solution and a plunger 305. The barrel 203 further comprises an outlet 309. The outlet 309 is preferably provided with a connection which allows mounting of the needle unit 322 to the outlet 309.

The injection needle unit 322 comprises a needle 307 and an ion exchange material 311. The needle unit 322 is adapted to be mounted on the syringe 301, preferably to a connection at the outlet 309 of the barrel 303. Such connections are known to a person skilled in the art, and comprises thread-screw mounts and bayonet mounts. The connection should allow for fluid connection between the barrel 303 and the needle unit 322. An ion exchange material 321 is preferably contained within the needle 307 to provide contact between a pharmaceutically acceptable solution and the ion exchange material 321 upon ejection of the pharmaceutically acceptable solution via the needle 307. The ion exchange material 321 should be capable of adjusting the pH of a pharmaceutically acceptable solution from a non-physiological pH to physiological pH upon contact between the ion exchange material 311 and the pharmaceutically acceptable solution.

The kit is adapted to be assembled, by connecting the injection needle unit 312 to the syringe 301, and to be provided with a pharmaceutically acceptable solution in the barrel 303 just prior to injection of the pharmaceutically acceptable solution.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

Therefore, it is intended that the invention not be limited to the particular embodiment disclosed as the best mode contemplated for carrying out this invention, but that the invention will include all embodiments falling within the scope of the appended claims.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

EXAMPLES

The invention is illustrated by way of the following, non-limiting examples. Table 1 briefly summarizes the experimental set-up of Examples 1-10, performed to illustrate the invention. The purpose of the experiments was to investigate the pH shift of pharmaceutically acceptable solution when contacted with different ion exchange materials:

TABLE 1

Overview of the examples performed to illustrate the invention.

| Example | Pharmaceutically acceptable solution used |
|---------|-------------------------------------------|
| 1 | Pharmaceutical acidic buffer |
| 2 | Pharmaceutical acidic buffer |
| 3 | Pharmaceutical acidic buffer |
| 4 | Pharmaceutical acidic buffer |
| 5 | Pharmaceutical acidic buffer |
| 6 | Anakinra |
| 7 | Anakinra |
| 8 | Pharmaceutical acidic buffer |
| 9 | Glycopressin |
| 10 | Somatropin |

Table 2 summarizes the different zeolites investigated in the Examples 1-10.

TABLE 2

Summary of the investigated zeolites.

| Trade namn | Producer | Notation | Counter ion | Sodium content (%) | Si/Al ratio |
|---|---|---|---|---|---|
| Faujasite | Merck KGaA | A | Calcium | 7.3 | 2 |
| 720KOA | Tosoh | B | Potassium | 1.3 | 18 |
| 500KOA | Tosoh | C | Potassium | 0.25 | 6.1 |
| 340NHA | Tosoh | D | Ammonium | 0.15 | 7 |
| 320NAA | Tosoh | E | Sodium | 12.5 | 5.5 |
| 642NAA | Tosoh | F | Sodium | 5 | 18 |
| 840NHA | Tosoh | G | Ammonium | <0.05 | 40 |
| CBV720 | Zeolyst | H | Hydrogen | 1.3 | 30 |
| CBV901 | Zeolyst | I | Hydrogen | 0.03 | 80 |
| CP814E | Zeolyst | J | Ammonium | 0.05 | 25 |
| ZEOflair110 | Zeochem | K | Sodium | 1.1 | 400 |
| CBV100 | Zeolyst | L | Sodium | 13 | 5.1 |
| CP811-300 | Zeolyst | M | Hydrogen | 0.05 | 300 |
| ZEOflair800 | Zeochem | N | Hydrogen | 4.3 | 800 |
| CPV10A | Zeolyst | O | Sodium | 6.5 | 13 |
| CBV400 | Zeolyst | P | Hydrogen | 2.8 | 5.1 |
| ZEOflair100 | Zeochem | Q | Sodium | 1.1 | 10 |

Example 1: Measurement of pH Shift

An aqueous buffer solution consisting of 10 mM sodium citrate, 125 mM sodium chloride, 0.1% (w/v) EDTA was used as test solution. The solution was aliquoted in a portion of 10 mL in a glass beaker at room temperature. The pH of the buffer solution was measured with a pH-meter to 6.50. A dry zeolite (aluminum silicate) powder was weighed and added to the aliquoted buffer and mixed by gentle stirring. The zeolite were added in an amount equal 0.1 gram/1 mL buffer. The resulting pH was measured after 5 minutes to be 8.63 and the positive shift in pH was recorded to 2.13.

CONCLUSION: The pH of a buffered aqueous solution can be increased by mixing with a zeolite powder.

Example 2: Measurements of pH Shift Using Different Zeolites

An aqueous buffer solution consisting of 10 mM sodium citrate, 125 mM sodium chloride, 0.1% (w/v) EDTA was used as test solution. The solution was aliquoted in portions of 10 or 4 mL in glass beakers at room temperature. The pH of the buffer solution was measured with a pH meter to be 6.25. Dry zeolite powders with different properties were weighed and added to the aliquoted buffer and mixed by gentle stirring. The zeolites were added in equal amounts: 0.1 gram/1 mL buffer. The resulting pH was measured after 5 minutes and the shift in pH was recorded. The results are shown in Table 3.

TABLE 3 pH shift for different zeolites.

| Zeolite | Counter ion | Na$_2$O content (%) | Si/Al ratio | pH shift |
|---|---|---|---|---|
| A | Calcium | 7.3 | 2 | 2.13 |
| B | Potassium | 1.3 | 18 | 0.36 |
| C | Potassium | 0.25 | 6.1 | 0.25 |
| D | Ammonium | 0.15 | 7 | −0.91 |
| E | Sodium | 12.5 | 5.5 | 0.04 |
| F | Sodium | 5 | 18 | 0.83 |
| G | Ammonium | <0.05 | 40 | −0.3 |
| H | Hydrogen | 1.3 | 30 | −2.47 |
| I | Hydrogen | 0.03 | 80 | −0.97 |
| J | Ammonium | 0.05 | 25 | −1.42 |
| K | Sodium | 1.1 | 400 | 2.42 |
| L | Sodium | 13 | 5.1 | 0.27 |
| M | Hydrogen | 0.05 | 300 | −0.82 |
| N | Sodium | 4.3 | 800 | 1.17 |
| O | Sodium | 6.5 | 13 | 3.21 |
| P | Hydrogen | 2.8 | 5.1 | −0.76 |
| Q | Sodium | 1.1 | 10 | 3.02 |

Example 3. pH Shift Over Time and Different Concentration of Ion Exchange Material An aqueous buffer solution consisting of 10 mM sodium citrate, 125 mM sodium chloride, 0.1% (w/v) EDTA was used as test solution. The solution was aliquoted in portions of 1 mL in glass beakers at room temperature. The pH of the buffer solution was measured with a pH-meter to be 6.25.

Dry zeolite powders with different properties were weighed and added to the aliquoted buffer and mixed by gentle stirring. The zeolites were added in varying amounts as shown in Table 2. The resulting pH was measured after 5 and 60 minutes, respectively and the shift in pH was recorded. The results are shown in Table 4.

TABLE 4 pH shift for different zeolites after 5 and 60 minutes, respectively.

| Zeolite | Counter ion | Na$_2$O content (%) | Si/Al ratio | Amount | pH shift 5 minutes | pH shift 60 minutes |
|---|---|---|---|---|---|---|
| A | Calcium | 7.3 | 2 | 10 mg | 0.04 | 0.04 |
| A | Calcium | 7.3 | 2 | 20 mg | 0.1 | 0.1 |
| A | Calcium | 7.3 | 2 | 30 mg | 0.17 | 0.17 |
| B | Potassium | 1.3 | 18 | 20 mg | 0.02 | 0.02 |
| F | Sodium | 5 | 18 | 20 mg | 0.21 | 0.21 |

It was concluded that the pH shift correlates with the amount of zeolite material. It was also seen that the pH shift is fast, occurring within 5 minutes.

Example 5. pH Shift of Solution Comprising Anakinra Over Time and Different Concentration of Ion Exchange Material An aqueous protein solution consisting of 150 mg/ml anakinra, 10 mM sodium citrate, 125 mM sodium chloride, 0.1% (w/v) EDTA was used as test solution.

The solution was aliquoted in portions of 0.7 mL in glass beakers at room temperature. The pH of the protein solution was determined using a pH-meter to 6.30.

Dry powder of zeolite A was weighed to 70 mg and added to the aliquoted protein solution and mixed by gentle stirring. The resulting pH was measured after 0.5, 1, 2, 3, 4 and 5 minutes and the shift in pH was recorded for each time point. The results are shown in Table 5.

TABLE 5 pH shift over time for anakinra.

| Zeolite | Counter ion | Na$_2$O content (%) | Si/Al ratio | Time (minutes) | pH-shift |
|---|---|---|---|---|---|
| A | Calcium | 7.3 | 2 | 0.5 | 0.15 |
| A | Calcium | 7.3 | 3 | 1 | 0.15 |
| A | Calcium | 7.3 | 4 | 2 | 0.37 |
| A | Calcium | 7.3 | 5 | 3 | 0.63 |
| A | Calcium | 7.3 | 6 | 4 | 0.73 |
| A | Calcium | 7.3 | 7 | 5 | 0.95 |

It was concluded that the positive pH shift for the protein solution is similar to the pH shift observed with pure buffer in Example 2, and that the positive pH-shift is fast but correlates with time.

Example 6. Protein Quality Measurement

An aqueous protein solution consisting of 150 mg/ml anakinra, 10 mM sodium citrate, 125 mM sodium chloride, 0.1% (w/v) EDTA was used as test solution. The solution was aliquoted in portions of 0.7 mL in polypropylene test tube at room temperature. The pH of the protein solution was measured with a pH-meter to 6.25.

Dry powders of zeolites with different properties were added to aliquoted protein solutions to a concentration of 50 mg/0.7 mL and incubated at 25 C for 2 hours. One aliquot of the protein solution was incubated without zeolite as control.

The protein quality and protein concentration of anakinra was determined by Size Exclusion Chromatography (SEC) HPLC and absorbance at 280 nm. The SEC-HPLC method was set up according to in-house standard protocol. A TSK-Gel G2000 SWXL 7.8 mm×30 cm column was used. The mobile phase was CSE Buffer, the injection volume/concentration was 100 µL/5 mg/mL, the wavelength was 280 nm, and the flow rate was 0.5 mL/min. The remaining monomer content of anakinra are presented in percentages. The results are presented in Table 6.

TABLE 6

Protein quality after zeolite treatment.

| Zeolite | Counter ion | Na$_2$O content (%) | Si/Al ratio | % Monomer | Protein conc (mg/mL) |
|---|---|---|---|---|---|
| NA | NA | NA | NA | 96.55 | 155 |
| F | Sodium | 5 | 18 | 96.52 | 157 |
| O | Sodium | 6.5 | 13 | 96.4 | 156 |
| Q | Sodium | 1.1 | 10 | 96.32 | 153 |
| A | Calcium | 7.3 | 2 | 96.3 | 156 |

It was concluded that the quality and concentration of the drug anakinra is not affected by the zeolite.

Example 7. pH Adjustment in a Syringe Comprising Ion Exchange Material

An aqueous protein solution consisting of 150 mg/ml anakinra, 10 mM sodium citrate, 125 mM sodium chloride, 0.1% (w/v) EDTA was used as test solution. The solution was aliquoted in portions of 0.7 mL in siliconized glass 1 mL prefillable syringe with an attached stainless steel needle. The syringe was closed by mounting a butyl rubber plunger at the open end of the syringe. The assembling was performed at room temperature. The pH of the protein solution was measured with a pH-meter to 6.34.

Dry Zeolite F powder was weighed added to aliquoted protein solutions to a concentration of 70 mg/0.7 mL and incubated at 25° C. for 3 minutes. The pH of the ejected protein solution from the syringe was recorded and the pH-shift noted, see table 7.

TABLE 7 pH measurements after pH adjustment in a syringe comprising an ion exchange material.

| Zeolite | Counter ion | Na$_2$O content (%) | Si/Al ratio | pH shift |
|---|---|---|---|---|
| F | Sodium | 5 | 18 | 0.12 |

Hence, ejecting a protein solution from a syringe containing a zeolite increases the pH of the protein solution.

Example 8. pH Adjustment in a Syringe Comprising Sintered Ion Exchange Material

An aqueous buffer solution consisting of 10 mM sodium citrate, 125 mM sodium chloride, 0.1% (w/v) EDTA was used as test solution. The pH of the buffer solution was measured with a pH meter to 6.59.

Dry zeolite powder (Q in Table 8) was weighed in a portion of 100 mg, placed between two stainless steel plugs. The powder was then sintered by increasing the pressure on the powder to 6 MPa and heating to 730° C. The resulting sintered zeolite powder cylinder had a diameter of 20 mm. The zeolite plug was pressed into the barrel of a polypropylene syringe barrel all the way to the front of the barrel. The buffer solution described above was filled with 5 mL from the rear end of the syringe. A rubber plunger was mounted in to the syringe. Pressure was applied on the rubber plunger and the buffer solution was forced to pass through the powder plug. The pH of the ejected solution from the syringe was recorded and the pH-shift was calculated as shown in table 8.

TABLE 8 pH measurements after pH adjustment in a syringe comprising a zeolite as ion exchange material.

| Zeolite | Counter ion | Na$_2$O content (%) | Si/Al ratio | pH-shift |
|---|---|---|---|---|
| Q | Sodium | 1.1 | 10 | 2.8 |

Hence, ejecting a buffered solution through a sintered zeolite cylinder in a syringe increases the pH.

Example 9. pH Adjustment of Glycopressin 1 mL of Glycopressin (1 mg/8.5 mL manufactured by Ferring) was aliquoted in a test tube. The pH of the solution was measured with a pH-meter to 3.74. Dry zeolite powder (Q) was weighed in a portion of 70 mg and added to the Glycopressin solution. The pH of the sample solution was then determined to be 5.92.

A new portion of the Glycopressin was aliquoted with 1 mL in a new test tube. The pH of the solution was measured with a pH-meter to 3.75. Dry Zeolite powder (Q) was weighed in a portion of 100 mg and added to the Glycopressin solution The pH of the sample solution was then determined to be 6.88.

Conclusion: The pH of the Glycopressin solution was increased by zeolite in a concentration dependent way.

Example 10. pH Adjustment of Somatatropin 0.5 mL of Somatatropin (Norditropin Simplex 10 mg/1.5 mL) manufactured by NovoNordisk was aliquoted in a test tube. The pH of the solution was measured with a pH-meter to 6.15. Dry zeolite powder (Q) was weighed in a portion of 50 mg and added to the somatropin solution The pH of the sample solution was determined to be 9.07

A new portion of the Somatropin was aliquoted with 0.5 mL in a new test tube. The pH of the solution was measured with a pH-meter to 6.22. Dry Zeolite powder (Q) was weighed in a portion of 19 mg and added to the somatropin solution The pH of the sample solution was then determined to be 7.28.

Conclusion: The pH of the Somatatropin solution was increased by zeolite in a concentration dependent way.

In the following, prophetic examples 11-18 are discussed.

Example 11. Sintered Zeolite Material in Needle

Zeolite material K is compressed into a porous plug using Spark Plug Sintering (SPS) technology. The zeolite powder is weighed into a cylindrical cavity with two open ends. The zeolite is compressed into a compact plug at a predefined pressure (100 to 1000 MPa) and sintered with pre-defined heat (500 to 1000° C.) into a porous mechanically stable plug. The cylindrical cavity may contain spikes parallel to the plug geometry to create channels of controlled diameters. The resulting plug is cooled and mounted into a female luer cone cannula hub with a stainless steel needle attached to the hub.

The cannula is mounted at the male luer part of a syringe. The syringe is filled with a pharmaceutical solution having a solution pH of 6.0. The open part of the syringe is closed with a rubber plunger. The rubber plunger is pushed forward and the pharmaceutical solution is transferred through the zeolite matrix in the hub and out through the needle. The pH of the ejected solution from the needle is 7.0.

Conclusion: The pH of the pharmaceutical solution is raised upon contact with the sintered zeolite material.

Example 12 Sintered Zeolite Material in Barrel

The porous zeolite plug of Example 11 is mounted at the front end of a glass or plastic syringe. A stainless steel needle is attached into the syringe end. The syringe is filled with a pharmaceutical solution having a solution pH of 6.0. The open part of the syringe is closed with a rubber plunger. The rubber plunger is pushed forward and the pharmaceutical solution is transferred through the zeolite matrix in the syringe and out through the needle. The pH of the ejected solution from the needle is 7.0.

Conclusion: The pH of the pharmaceutical solution is raised upon contact with the sintered zeolite material.

Example 13. Zeolite Material Immobilized on Support in Needle

Zeolite material K is immobilized on a porous titanium oxide, aluminum or mullite support or similar. The immobilization is performed by making a suspension of the zeolites in distilled water and having it nucleate on the support creating a porous membrane.

The resulting membrane is mounted into a female luer cone cannula hub with a stainless steel needle attached to the hub. The cannula is mounted at the male luer part of a syringe. The syringe is filled with a pharmaceutical solution having a solution pH of 6.0. The open part of the syringe is closed with a rubber plunger. The rubber plunger is pushed forward and the pharmaceutical solution is transferred through the zeolite matrix in the hub and out through the needle. The pH of the ejected solution from the needle is 7.0.

Conclusion: The pH of the pharmaceutical solution is raised upon contact with the immobilized zeolite material.

Example 14. Zeolite Material Immobilized on Support in Barrel

The porous zeolite membrane of Example 13 is mounted at the front end of a glass or plastic syringe. A stainless needle is attached into the syringe end.

The syringe is filled with a pharmaceutical solution having a solution pH of 6.0. The open part of the syringe is closed with a rubber plunger. The rubber plunger is pushed forward and the pharmaceutical solution is transferred through the zeolite matrix in the syringe and out through the needle. The pH of the ejected solution from the needle is 7.0.

Conclusion: The pH of the pharmaceutical solution is raised upon contact with the immobilized zeolite material.

Example 15. Zeolite/Polymer Membrane in Needle

PVDF (polyvinylidene difluoride) is dissolved in NMP (N-Methyl-2-pyrrolidone) solvent to a solution. Zeolite material K is suspended in the PVDF/NMP solution by mixing for 5 hours at room temperature. The resulting suspension is distributed over a glass plate. The glass plate is immersed in distilled water to solidify into a membrane. The resulting membrane is mounted into a female luer cone cannula hub with a stainless steel needle attached to the hub.

The cannula is mounted on a the male luer part of a syringe. The syringe is filled with a pharmaceutical solution having a solution pH of 6.0. The open part of the syringe is closed with a rubber plunger. The rubber plunger is pushed forward and the pharmaceutical solution is transferred through the zeolite matrix in the hub and out through the needle. The pH of the ejected solution from the needle is 7.0.

Conclusion: The pH of the pharmaceutical solution is raised upon contact with the zeolite/polymer material.

Example 16. Zeolite/Polymer Membrane in Barrel

The porous zeolite membrane of Example 15 is mounted at the front end of a glass or plastic syringe. A stainless steel needle is attached into the syringe end. The syringe is filled with a pharmaceutical solution having a solution pH of 6.0. The open part of the syringe is closed with a rubber plunger. The rubber plunger is pushed forward and the pharmaceutical solution is transferred through the zeolite matrix in the syringe and out through the needle.

Conclusion: The pH of the pharmaceutical solution is raised upon contact with the zeolite/polymer material.

Example 17. Zeolite Powder in Needle

Powder of zeolite K is contained in a cylindrical container. The container is made from polymer or metallic materials where the base and top of the cylinder is permeable to water. The container with the zeolite powder is mounted into a female luer cone cannula hub with a stainless steel needle attached to the hub.

The cannula is mounted at the male luer part of a syringe. The syringe is filled with a pharmaceutical solution having a solution pH of 6.0. The open part of the syringe is closed with a rubber plunger. The rubber plunger is pushed forward and the pharmaceutical solution is transferred through the cylindrical with the zeolite in the hub and out through the needle. The pH of the ejected solution from the needle is 7.0.

Conclusion: The pH of the pharmaceutical solution is raised upon contact with the powder zeolite material.

Example 18. Zeolite Powder in Needle

The cylindrical container with zeolite powder is mounted at the front end of a glass or plastic syringe. A stainless steel needle is attached. The syringe is filled with a pharmaceutical solution having a solution pH of 6.0. The open part of the syringe is closed with a rubber plunger. The rubber plunger is pushed forward and the pharmaceutical solution is transferred through the cylindrical container in the syringe and out through the needle. The pH of the ejected solution from the needle is 7.0.

Conclusion: The pH of the pharmaceutical solution is raised upon contact with the powder zeolite material.

The invention claimed is:

1. A syringe comprising a barrel and a plunger, the barrel having an interior volume adapted to contain a liquid pharmaceutical composition having a first, non-physiological pH, wherein the syringe further comprises an ion exchange material provided within the syringe such that it is not in fluid communication with the interior volume of the barrel, and wherein the ion exchange material is provided at a position to, in use, allow contact with the liquid pharmaceutical composition upon ejection of the liquid pharmaceutical composition from the barrel, wherein the ion exchange material is insoluble and/or immiscible in the liquid pharmaceutical composition and is adapted to, upon contact with the liquid pharmaceutical composition, adjust the pH of the liquid pharmaceutical composition from the first, non-physiological pH to a second pH, wherein the first, non-physiological pH is in the range of 3-6.6 and the second pH is in the range of 7.0-8.0, wherein the second pH is higher than the first non-physiological pH.

2. The syringe according to claim 1, further comprising an injection needle mounted in fluid communication with an outlet of the barrel, wherein the ion exchange material is provided within the injection needle.

3. The syringe according to claim 1, wherein the ion exchange material is a solid porous material, configured to allow the liquid pharmaceutical composition to flow through the solid porous material.

4. The syringe according to claim 3, wherein the solid porous material comprises a material selected from a zeolite material loaded with $Na^+$, $H^+$ and/or $Ca^{2+}$, a polystyrene material, and mesoporous silica.

5. A pre-filled syringe comprising a barrel and a plunger, the barrel having an outlet, the barrel containing a liquid pharmaceutical composition having a first, non-physiological pH, wherein the syringe further comprises an ion exchange material provided such that the liquid pharmaceutical composition, when contained within the barrel, does not contact the ion exchange material, and wherein the ion exchange material is provided at a position to allow contact with the liquid pharmaceutical composition upon ejection of the liquid pharmaceutical composition from the barrel via the outlet, wherein the ion exchange material is insoluble and/or immiscible in the liquid pharmaceutical composition and is adapted to, upon contact with the liquid pharmaceutical composition, adjust the pH of the liquid pharmaceutical composition from the first, non-physiological pH to a second pH, wherein the first, non-physiological pH is in the range of 3-6.6 and the second pH is in the range of 7.0-8.0, wherein the second pH is higher than the first non-physiological pH.

6. The pre-filled syringe according to claim 5, wherein the pre-filled syringe comprises a separator arranged at a position along an ejection path from the barrel, and wherein the liquid pharmaceutical composition is present upstream of said separator along said ejection path, and the ion exchange material is provided downstream of said separator along said ejection path, and the separator is adapted to in a first state prevent the liquid pharmaceutical composition from contacting the ion exchange material, and adapted to in a second state allow fluid communication between the liquid pharmaceutical composition and the ion exchange material.

7. The pre-filled syringe according to claim 5, wherein the syringe comprises an injection needle mounted in fluid communication with said outlet.

8. The pre-filled syringe according to claim 7, wherein the ion exchange material is contained within said needle.

9. The pre-filled syringe according to claim 5, wherein the ion-exchange material comprises a porous solid material.

10. The pre-filled syringe according to any claim 9, wherein the porous solid material comprises a material selected from a zeolite material, a polystyrene material, and mesoporous silica.

11. The pre-filled syringe according to claim 10, wherein the porous solid material comprises a zeolite material, wherein the zeolite is an aluminosilicate zeolite material loaded with $Na^+$, $H^+$ and/or $Ca^{2+}$ having a $SiO_2/Al_2O_3$ molar ratio above 1.5; and/or a $Na_2O$ content below 10 wt-% of the total zeolite weight.

12. The pre-filled syringe according to claim 5, wherein the liquid pharmaceutical composition comprises an acidic buffer solution.

13. The pre-filled syringe according to claim 5, wherein the liquid pharmaceutical composition comprises a protein drug or peptide drug.

14. The pre-filled syringe according to claim 13, wherein the protein or peptide drug is an IL-1 receptor antagonist.

15. The pre-filled syringe according to claim 14, wherein the IL-1 receptor antagonist is anakinra.

* * * * *